(12) United States Patent
Elghazzawi et al.

(10) Patent No.: US 12,728,277 B2
(45) Date of Patent: Sep. 8, 2026

(54) DISPLAY FOR DUAL-MODE MEDICAL DEVICE

(71) Applicant: ZOLL Medical Corporation, Chelmsford, MA (US)

(72) Inventors: Ziad F. Elghazzawi, Newton, MA (US); John Kubat, Townsend, MA (US); Frederick Faller, Burlington, MA (US); Jing Pan, Waban, MA (US); Peter A. Lund, Nashua, NH (US)

(73) Assignee: ZOLL Medical Corporation, Chelmsford, MA (US)

( * ) Notice: Subject to any disclaimer, the term of this patent is extended or adjusted under 35 U.S.C. 154(b) by 300 days.

(21) Appl. No.: 17/681,969

(22) Filed: Feb. 28, 2022

(65) Prior Publication Data

US 2022/0409913 A1 Dec. 29, 2022

Related U.S. Application Data

(63) Continuation of application No. 16/730,348, filed on Dec. 30, 2019, now Pat. No. 11,291,851, which is a (Continued)

(51) Int. Cl.
*A61N 1/39* (2006.01)
*G09G 3/00* (2006.01)

(52) U.S. Cl.
CPC ......... *A61N 1/3993* (2013.01); *A61N 1/3925* (2013.01); *A61N 1/3968* (2013.01); *G09G 3/035* (2020.08)

(58) Field of Classification Search
CPC ............................ A61N 1/3993; A61N 1/3925
(Continued)

(56) References Cited

U.S. PATENT DOCUMENTS 5,736,233 A 4/1998 Fye
6,021,349 A 2/2000 Arand et al.
(Continued)

FOREIGN PATENT DOCUMENTS

JP 10066736 3/1998
JP 2004512909 4/2004
(Continued)

OTHER PUBLICATIONS

Chinese Office Action, with English Translation, Application No. 201080054200.5, dated May 5, 2014. 10 pages.
(Continued)

*Primary Examiner* — Nicole F Johnson
(74) *Attorney, Agent, or Firm* — Secant IP, P.L.L.C.

(57) ABSTRACT

A medical device includes a display area that has a thin panel having a substantially flat front surface portion, a translucent layer on a back surface of the thin panel, a layer of text or graphics on a back surface of the translucent layer, and arranged so that the text or graphics is not visible to a user on the front side when light is not provided from inside the device housing, a switch to allow a user to select a first mode or a second mode for the device, and circuitry arranged to energize one or more light sources to provide light from behind the thin panel when the device is in the first mode, and to thereby make visible the text or graphics when the device is in the first mode.

20 Claims, 5 Drawing Sheets

Related U.S. Application Data continuation of application No. 16/140,581, filed on Sep. 25, 2018, now Pat. No. 10,556,120, which is a continuation of application No. 15/081,298, filed on Mar. 25, 2016, now Pat. No. 10,112,055, which is a continuation of application No. 12/956,836, filed on Nov. 30, 2010, now Pat. No. 9,308,384.

(60) Provisional application No. 61/265,309, filed on Nov. 30, 2009.

(58) Field of Classification Search
USPC .............................................................. 607/5
See application file for complete search history.

(56) References Cited

U.S. PATENT DOCUMENTS

| | | | | |
|---|---|---|---|---|
| 6,339,421 | B1 | 1/2002 | Puckeridge | |
| 6,356,785 | B1 | 3/2002 | Snyder et al. | |
| 6,754,526 | B2 | 6/2004 | Daynes et al. | |
| 7,230,231 | B2 | 6/2007 | Keller et al. | |
| 7,394,459 | B2 | 7/2008 | Bathiche et al. | |
| 7,454,269 | B1 | 11/2008 | Dushane et al. | |
| 7,600,880 | B2 | 10/2009 | Cybart et al. | |
| 7,651,235 | B2 | 1/2010 | Seki | |
| 7,672,720 | B2 | 3/2010 | Heath | |
| 7,804,484 | B2 | 9/2010 | Martinez et al. | |
| 8,165,671 | B2 | 4/2012 | Freeman et al. | |
| 8,201,102 | B2 | 6/2012 | Lee et al. | |
| 9,308,384 | B2 | 4/2016 | Elghazzawi et al. | |
| 10,112,055 | B2 | 10/2018 | Elghazzawi et al. | |
| 10,556,120 | B2 | 2/2020 | Elghazzawi et al. | |
| 11,291,851 | B2 | 4/2022 | Elghazzawi et al. | |
| 2002/0072774 | A1* | 6/2002 | Daynes | A61N 1/3904 607/5 |
| 2005/0131465 | A1* | 6/2005 | Freeman | A61N 1/3625 607/5 |
| 2006/0025824 | A1 | 2/2006 | Freeman et al. | |
| 2006/0069326 | A1 | 3/2006 | Heath | |
| 2006/0109258 | A1 | 5/2006 | Takisawa | |
| 2006/0250371 | A1 | 11/2006 | Martinez et al. | |
| 2007/0285913 | A1 | 12/2007 | Cybart et al. | |
| 2007/0299473 | A1* | 12/2007 | Matos | A61N 1/3904 607/9 |
| 2009/0064013 | A1 | 3/2009 | Lee et al. | |
| 2009/0122232 | A1 | 5/2009 | Seki | |
| 2011/0130798 | A1 | 6/2011 | Elghazzawi et al. | |
| 2016/0271409 | A1 | 9/2016 | Elghazzawi et al. | |
| 2019/0022401 | A1 | 1/2019 | Elghazzawi et al. | |
| 2020/0316395 | A1 | 10/2020 | Elghazzawi et al. | |

FOREIGN PATENT DOCUMENTS

| | | | |
|---|---|---|---|
| JP | 2005524498 | 8/2005 | |
| JP | 2008523878 | 7/2008 | |
| JP | 2009-028402 | 2/2009 | |
| JP | 2010-500144 | 1/2010 | |
| WO | WO-2009060374 A2 * | 5/2009 | A61B 5/363 |

OTHER PUBLICATIONS

Chinese Office Action, with English Translation, Application No. 201080054200.5, dated Apr. 3, 2017 7 pages.

EP Office Action, Application No. 10834058.9, dated Mar. 12, 2015.

International Search Report & Written Opinion for Application No. PCT/US2010/058434, dated Feb. 7, 2011. 8 pages.

International Preliminary Report on Patentability for Application No. PCT/US2010/058434, dated Jun. 14, 2012. 8 pages.

Japanese Office Action, with English Translation, Application No. 2012-541230, mailed Sep. 10, 2014. 3 pages.

Supplementary European Search Report, EP10834058, mailed Apr. 18, 2013. 7 pages.

* cited by examiner

DISPLAY FOR DUAL-MODE MEDICAL DEVICE

CROSS-REFERENCE TO RELATED APPLICATIONS

This application claims benefit under 35 U.S.C. § 120 as a continuation of U.S. application Ser. No. 16/730,348, filed Dec. 30, 2019, which claims benefit under 35 U.S.C. § 120 as a continuation of U.S. application Ser. No. 16/140,581, filed Sep. 25, 2018, now U.S. Pat. No. 10,556,120, which claims benefit under 35 U.S.C. § 120 as a continuation of U.S. application Ser. No. 15/081,298, filed Mar. 25, 2016, now U.S. Pat. No. 10,112,055, which claims benefit under 35 U.S.C. § 120 as a continuation of U.S. application Ser. No. 12/956,836, filed Nov. 30, 2010, now U.S. Pat. No. 9,308,384, which claims priority under 35 U.S.C. § 119(e) to provisional Application No. 61/265,309, filed Nov. 30, 2009, each of which is hereby incorporated herein by reference in its entirety.

TECHNICAL FIELD

This document relates to components for creating a user display on a medical device such as a defibrillator.

BACKGROUND

Sudden cardiac arrest (colloquially "a heart attack") is a serious condition that frequently results in death. The speed with which life saving personnel can respond to a sudden cardiac arrest is one of the most important, if not the most important, determinant of a successful outcome for a victim of sudden cardiac arrest. For example, it is said that likelihood of surviving a sudden cardiac arrest falls ten percent for every minute in which assistance (e.g., defibrillation or chest compressions) is delayed. As a result, speed of response can be very important to a heart attack victim.

One typical mode of treatment for sudden cardiac arrest is to "shock" the heart back into a steady beating pattern using an external defibrillator. Such a defibrillator commonly includes a pair of electrodes that are placed on the victim's chest and are connected electrically to a power unit. In hospitals, such a defibrillator is typically used by a "code team" that responds to "codes" issued by attending caregivers. Such teams use advanced defibrillators that they can control for a number of parameters, such as by displaying a patient's ECG and blood oxygen level, and by letting caregivers set the power level to be delivered to the victim and provide pacing inputs.

Such professional defibrillators, known as Advanced Life Support, or ALS, defibrillators can be intimidating for other staff, including medically-trained staff such as shift nurses. As a result, a patient may have to wait for a code team to arrive even though an otherwise-competent caregiver is nearby.

SUMMARY

This document describes systems and techniques that may be used to provide a dual-mode external defibrillator. In one mode, the defibrillator may be used as an ALS defibrillator, and in another mode, it may be used as a Basic Life Support, or BLS, defibrillator. The different modes present substantially different "looks" to a user, where the BLS mode provides a simplified device or interface, as compared to the ALS mode.

Certain indicators that are lit by the defibrillator and are visible from the front of the defibrillator may be concealed during BLS mode so that a caregiver with a lower level of training will not be distracted or intimidated by such indicators. The indicators may include, for example, lights that indicate whether the defibrillator is currently analyzing a patient's readings and/or is charging a defibrillator circuit. The indicators may also be integrated with buttons on the device, so that the user can see that the buttons are available for selection when the device is in ALS mode, but not see the buttons at all (and the buttons are not available for selection) when in BLS mode. Such selective display of the indicators can be provided using a specially printed label between the front surface of the defibrillator and light sources that back-light the label. Specifically, text or graphics can be "dead fronted" by placing a layer having a comparatively dark translucent ink on it in line with the text or graphics on another layer. In this manner, the text or graphics is hidden from being seen from the front of the device until substantial light is provided from behind the text and graphics, from inside the defibrillator housing. LEDs placed inside the housing may be connected so as to be energized when the defibrillator is in ALS mode, so that the enhanced ALS capabilities of the device can be announced simultaneously to a user.

Implementations of these features may provide for one or more advantages. For example, BLS capabilities may be provided conveniently in a hospital setting so that immediate on-site caregivers can provide immediate defibrillation to a patient who suffers a sudden cardiac arrest. The further capabilities of an ALS mode, including physical adjustment mechanisms, may be hidden in BLS mode so that such a caregiver may readily provide therapy to a patient, and not be distracted by options that are not of interest to them. Also, a single defibrillator may be used for both BLS and ALS purposes. As a result, a hospital need not buy or store as many defibrillators, and a ward will be less cluttered with equipment, so that the defibrillator can be kept closer to a patient as a result (though the hospital may purchase more defibrillators in the end, if they become particular useful. Also, the defibrillator may provide both BLS and ALS functionality, and may switch between the two modes essentially seamlessly. For example, a shift nurse could start a defibrillator in BLS mode and provide immediate care to a patient suffering from sudden cardiac arrest, and when the code team arrives, it could switch the unit to ALS mode for more detailed treatment of the patient. Such a switchover can be achieved without having to remove and replace electrodes that the initial caregiver applied, so that the patient can receive basic care very quickly and can shift to more advanced care quickly also. As a result, the patient's chance of survival may be maximized.

In one implementation, a multi-mode electronic medical device is disclosed that comprises a device housing that defines a front side of the device that is positioned to be visible to a user of the device during use of the device, a display area comprising a thin panel having a substantially flat front surface portion along the front side of the device, and a translucent layer behind, and aligned with, the thin panel. The device also comprises a layer of text or graphics behind, and aligned with the translucent layer, and arranged so that the text or graphics is not visible to a user on the front side of the device when light is not provided from inside the device housing, and a switch to allow a user to select a first mode or a second mode for the device. Moreover, the device comprises circuitry arranged to energize one or more light sources to provide light from behind the thin panel when the device is in the first mode, and to thereby make visible the text or graphics when the device is in the first mode.

The first mode can be an advanced life support mode and the second mode can be a basic life support mode for a defibrillator. The translucent layer can include a velvet textured polyester film. Also, the switch can be connected to be operated by user by a physical knob that may be grasped by the user and that is located adjacent to the display area. Moreover, the display area can be made visible to a user of the device in the first mode and the second mode, but text is visible in the display area only in the first mode.

In some aspects, the device also includes one or more push button switches positioned behind the thin panel, and wherein the thin panel is flexible to permit a user to depress the one or more push button switches by pressing on the thin panel. The switches can be mounted directly to a circuit board that is located inside the housing and behind the thin panel. The device can also include a plurality of light emitting diodes mounted to the circuit board, aligned to provide light though the layer of text or graphics, and controlled to be lit only when the device is in the first mode. In addition, the device can comprise a front panel frame that supports the thin layer and defines a plurality of opaque compartments, wherein each opaque compartment corresponds to a portion of the thin layer that overlies the opaque compartment and that is substantially light tight from others of the opaque compartments so that lighting of one compartment does not result in lighting of other compartments. And is certain aspects, the circuitry comprises a microprocessor and associated memory programmed to provide advanced life support functionality with the device when the device is in the first mode, and to provide basic life support functionality and to de-energize the one or more light sources when device is in a second mode.

In another implementation, a method of operating a multi-mode defibrillator is disclosed. The method comprises receiving a user input to operate the defibrillator in a basic mode, interacting with the user without energizing lights for showing advanced features of the defibrillator, receiving a user input to operate the defibrillator in an advanced mode, lighting light sources through a layer of printed text or graphics, a translucent layer, and a thin transparent or translucent face layer that is arranged so that the text or graphics is not visible to a user of the defibrillator when the light sources are not lit, and interacting with a user in the advanced mode. The user input can be received by turning a switch from a first position to a second positions. The method can also include receiving one or more user contacts with areas in which light is provided by the light sources, actuating switches in response to the user contacts, and altering operation of the defibrillator in the advanced mode in response to actuating the switches.

In some aspects, the actuated switches are mounted directly to a circuit board that is located inside a housing of the defibrillator and behind the printed text or graphics. Also, the light sources can be lit under the control of a microprocessor and associated memory programmed to provide advanced life support functionality with the defibrillator when the defibrillator is in the advanced mode, and to provide basic life support functionality and to de-energize the one or more light sources when defibrillator is in the basic mode.

In another implementation, a multi-mode external defibrillator is disclosed that comprises a defibrillator housing having a front side, and defining a front face that faces the front side and is positioned to be visible to a user of the defibrillator during use of the defibrillator, and a display area comprising a thin panel having a substantially flat front surface portion that faces the front side. The defibrillator also includes a switch to allow a user to select a first mode or a second mode for the defibrillator, circuitry arranged to energize one or more light sources to provide light from behind the thin panel when the defibrillator is in the first mode and means for preventing text or graphics in the display are from being visible to a user of the defibrillator while the defibrillator is in the second mode, but to make the text or graphics in the display visible to the user while the defibrillator is in the first mode.

The details of one or more embodiments are set forth in the accompanying drawings and the description below. Other features and advantages will be apparent from the description and drawings, and from the claims.

DETAILED DESCRIPTION

This document describes mechanisms by which a medical external defibrillator can provide interaction in both a BLS mode and an ALS mode. The techniques described here provide for convenient operation in BLS mode so that a relatively untrained user can operate the defibrillator. For example, features that may be desirable in an ALS mode can be hidden from a user in the BLS mode so that the user is not overwhelmed or confused. Certain such features may be manifested by physical objects that a user may manipulate to affect the operation of the defibrillator, and because they are physical, they must be concealed physically (e.g., by placing a cover over them) rather than electronically (e.g., by not displaying them on a screen).

As one example, certain notification or warning messages can be hidden from a user of a defibrillator when the defibrillator is in BLS mode. Those messages may simply indicate a status of the defibrillator, and can also represent buttons that a user may select on the defibrillator when it is in ALS mode but not when it is in BLS mode. Also, certain physical controls can be covered when the defibrillator is in BLS mode, such as knobs that a user turns to adjust the energy level delivered by the defibrillator—such knobs may have no meaning to a caregiver who is not especially trained for emergency life support. A latching mechanism for a door that covers the knobs may be connected to a mechanism that is used to switch the defibrillator from BLS mode to ALS mode (or, for example, to a pacing mode within ALS mode), so that the latching mechanism is caused to "kick" the door open and out of the way when the switching mechanism is moved by a user (e.g., by a highly trained caregiver who is taking over from a less-trained caregiver). Both of these mechanisms—electronic transitions and mechanical transitions—may be used to provide a convenient, and essentially automatic, transition from partly-featured BLS mode to fully-features ALS mode.

Figures 1A, 1B:
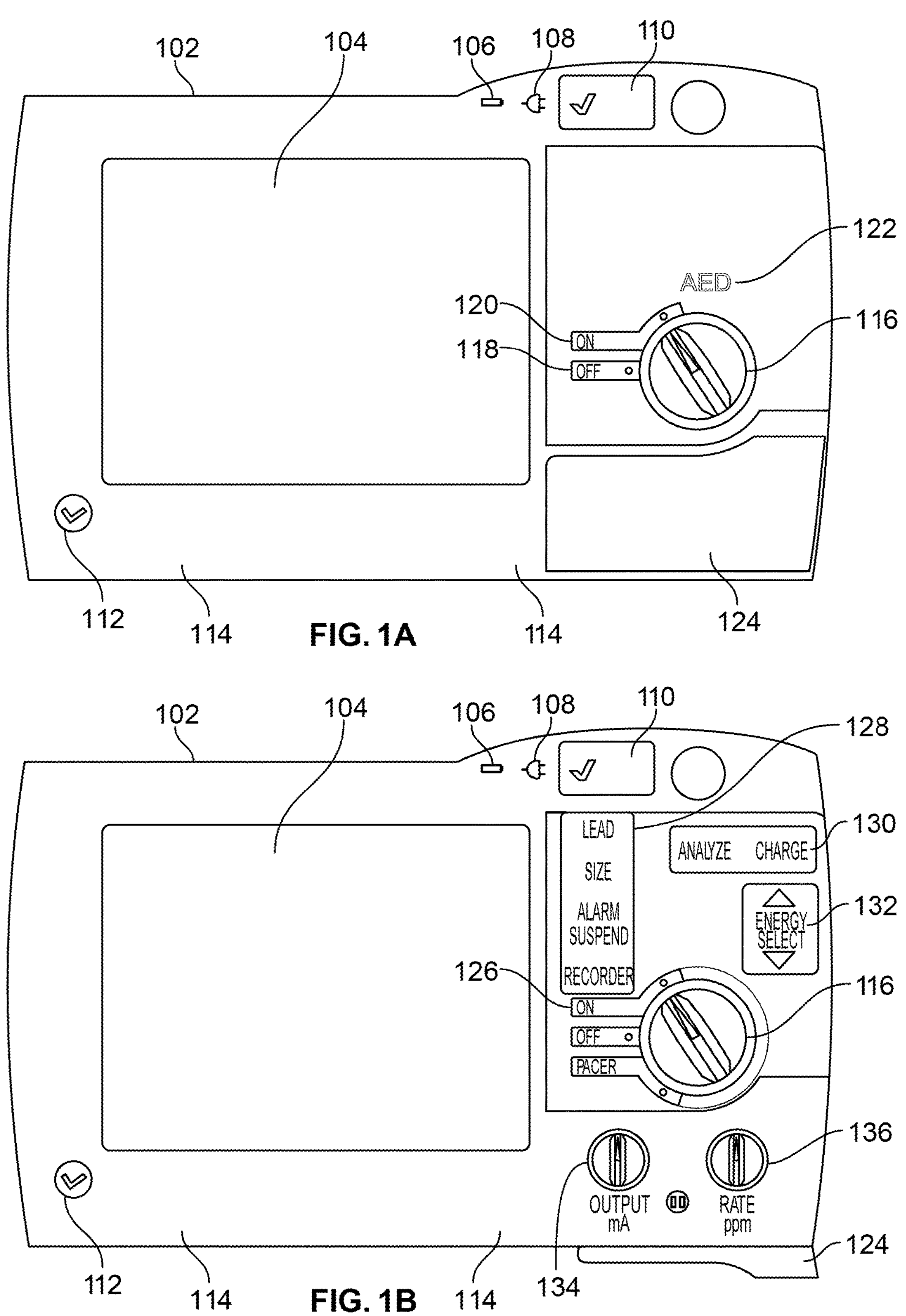
FIG. 1A shows a front of a dual-mode defibrillator in Basic Life Support mode.
FIG. 1B shows a front of a dual-mode defibrillator in advanced life support mode.

FIG. 1A shows a front of a dual-mode defibrillator 102 in basic life support mode. FIG. 1B shows a front of the same dual-mode defibrillator 102 in advanced life support mode. Each figures shows the front surface of the defibrillator 102, with a number of features that can be seen by a caregiver when they are operating the defibrillator 102. The status or mode of the defibrillator 102 can be seen by a user, for example, from indicator 122 in FIG. 1A, where it is indicated that the device is on and is usable as an automated external defibrillator, or AED, which is a BLS mode. In FIG. 1B, many additional indicators and controls are shown, as the device has been changed to an ALS with Pacer mode by rotating knob 116 counterclockwise two spots to the "PACER" indication.

Referring now more specifically to items that are visible under both modes for the defibrillator 102, there is shown an electronic display 104, which may take the form of a cathode ray tube (CRT), liquid crystal display (LCD) panel, organic light emitting diode (OLED) panel, or other appropriate electronic display technology, that is preferably capable of providing both textual and graphical information to a user of the defibrillator 102 in a dynamic manner. In BLS mode, for example, the display 104 may be relatively unadorned, and may provide text to guide a user through the process of providing life support to a victim. For example, the display 104 may instruct the user textual or via simplified graphics to apply electrodes to the patient, to perform CPR, and to push harder or softer, or faster or slower, as the case may be, when they are providing chest compressions to the victim (as sensed, e.g., via an accelerometer that is provided in an assembly with the electrodes, and that the user push, within a housing, against the victim's chest when delivering chest compressions). Such instructions on the display 104 may also be accompanied by verbal instructions provided by a speaker in the defibrillator 102. The unit may enter BLS mode automatically when it is powered up, and then may be changed to ALS mode (and pacing mode) by an user.

In ALS mode, the display 104 may provide additional, and sometimes very detailed, information to the user. For example, the display may shown a ECG for the patient, a graph of CPR chest compressions over a past set period of time, the total elapsed time of performing CPR, the victim's pulse, and information about the electrode pads applied to the patent.

In addition, the lower edge of the display 104 may exhibit textual or graphical labels that correspond to a row of selection keys 114 (soft keys) that are arrayed below the display 104. Thus, for example, the row of labels may make up a menu of topics that a user may select by pressing an associated aligned key in order to see additional information about the defibrillator 102, or to change parameters for controlling the defibrillator 102.

Next to the selection keys 114 is an non-invasive blood pressure (NIBP) button 112. Selection of this button may allow the defibrillator 102 to measure a victim's blood pressure, which may in turn be shown on the display 104.

A number of additional indicators are displayed in both modes along the top of the defibrillator 102. For example, a battery indicator 106 may be made to light or blink to indicate to a user when battery reserve power is running low, so that the user may adjust their treatment of a victim accordingly or can seek out an AC power source for the defibrillator 102. Also, the battery level may be shown on an icon, such as by showing the image of the battery being "filled" to a degree that corresponds to the level of remaining battery power, a technique that is familiarly used on cellular telephones. In one implementation, a steady yellow indicator shows that the battery is charging, a steady green indicator shows that the battery is charged, and an alternating yellow and green indicator shows that no battery is installed or there is a battery charging fault.

In a similar manner, an AC power indicator 108 may be lit when the defibrillator 102 is plugged into an AC power source. The indicator may be visible, but not lit, when the defibrillator 102 is not plugged in, so that a user of the defibrillator 102 can know about the ability to plug the defibrillator 102 into a power source.

A code readiness indicator 110 is lit when the defibrillator 102 is ready for operation, based on a most recent self-diagnostic run. A green check mark indicates that the unit is ready for therapeutic use, while a red "X" indicates the defibrillator's 102 readiness is compromised and that it may not be ready for therapeutic use.

A mode selector knob 116 can be grasped by a user of the defibrillator 102 and rotated to select a mode in which to operate the defibrillator 102. The knob may typically be located in an "OFF" position (as indicated by an arrow indicator on a spine of the knob 116). In FIG. 1A, the knob has been turned clockwise by a user to point toward an "ON" position, in which the defibrillator 102 operates as an semi-automatic AED, as indicated by AED indicator 122.

As can be seen in FIG. 1A, the user interface in this BLS mode is very spartan. A user is expected in such a mode not to have substantial training, and thus not to need precise control over the defibrillator 102. Thus, the display 104 may provide sufficient direction to the user, perhaps in combination with audible instructions. Also, in this example, the user is not even shown an option for another mode to which to turn the defibrillator 102.

In FIG. 1B, the user has rotated the knob 116 counterclockwise past the "OFF" position, to a heretofore hidden "PACER" position, which may be part of a manual ALS mode for the defibrillator 102. A user who would want to be able to use an ALS mode and would be capable of using such a mode may be presumed to have been highly trained and thus to have been very familiar with the defibrillator 102 and know that the mode is available (though the mode could be indicated on the defibrillator 102 also).

A number of changes can be seen to have occurred in response to the user changing the mode to the ALS mode. For example, a display area above the knob 116 appeared blank when the defibrillator 102 was in BLS mode. Now, however, with the defibrillator 102 in ALS mode, the display area has a number of labels that are visible on it, because, when the user switched the knob 116 to ALS mode, a microprocessor and related circuitry in the device enabled a number of features that are relevant to a highly-trained rescuer, but are not relevant to a less trained rescuer. For example, the display area may show information, including in user-selectable areas, for parameters relating to the level of energy applied to the defibrillator 102 electrodes, and relating to reading of, and control of, ECG-related functions.

Also, a pacer cover 124 that previously covered two adjustment knobs 134, 136 in the lower corner of the defibrillator 102 has pivoted downward and below the defibrillator 102 housing so as to expose the knobs 134, 136.

Knob 134 controls the power output of electrodes attached to the defibrillator 102 when they provide a pacing output. Knob 136, when pacing is selected, sets the rate (pulses per minute) at which the pacemaker will operate. The selected pace rate setting is then indicated on the display 104.

The defibrillator 102 may also be provided with additional components that are not visible in these views of the front of the defibrillator. For example, packaged electrodes and associated feedback mechanisms (e.g., a accelerometer-based displacement measurement system) may be attached physically to the side of the defibrillator 102 and may be pre-attached electrically to the defibrillator 102 so as to permit faster deployment of the defibrillator 102 in an emergency situation. Also, a strip chart recorder may be included inside the housing for the defibrillator 102, as may electronic recording mechanisms and components for transferring the electronic data, such as a USB port, WiFi wireless interface, and the like.

Figures 2A, 2B, 2C:
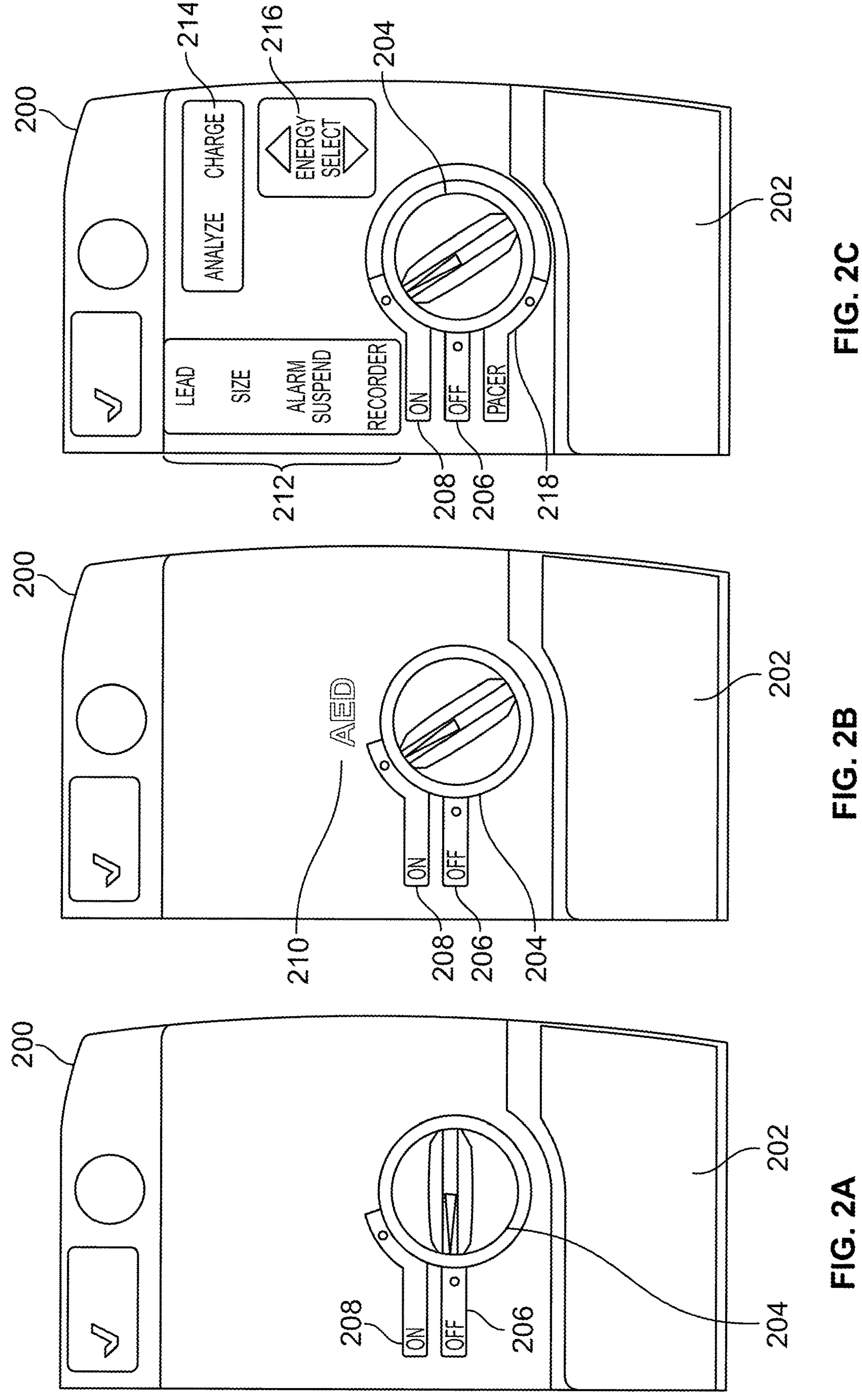
FIG. 2A shows a control panel of a dual-mode defibrillator in the off position.
FIG. 2B shows a control panel of a dual-mode defibrillator in automatic mode.
FIG. 2C shows a control panel of a dual-mode defibrillator in manual mode.

FIG. 2A shows a control panel of a dual-mode defibrillator in the off position. FIG. 2B shows a control panel of a dual-mode defibrillator in automatic mode. FIG. 2C shows a control panel of a dual-mode defibrillator in manual pacing mode. In general, these figures show the control panel area of the defibrillator 102 shown in FIGS. 1A and 1B, when the defibrillator 102 is off, in AED or BLS mode, and manual or ALS mode with pacing, respectively.

Referring to FIG. 2A, a mode setting knob 204 is directed to an "OFF" position 206. In this position, the defibrillator is powered off, and only standard automatic diagnostic features are enabled on the defibrillator. Also, a display area above the knob 204 is blank, and a pacing cover 202 is closed across the front of the defibrillator.

In FIG. 2B, the knob 204 has been turned clockwise by a user of the defibrillator to the "ON" position. As a result, an indicator on the display area has been lit so as to show text that has been printed behind a front surface of the display area with the letters "AED." Such text is intended to communicate that the defibrillator is operating, in that mode, as an automatic external defibrillator. The pacing cover 202 is also still closed, as a user of an AED need not take advantage of such functionality, and would likely be confused regarding what they are supposed to do with it, if it were shown to them. Thus, this view of the control panel for a user of the device in BLS or AED mode is simple, so that the user can focus on providing basic care for a victim, until more advanced caregivers arrive.

In FIG. 2C, a user has switch the defibrillator to ALS mode with pacing (though the knob 204 is still shown as pointing to the "ON" position, and would typically switch to ALS before the or when the user rotates the knob 204 counterclockwise so that it points to the "PACER" position).

In this mode, an "ENERGY SELECT" indicator 216 is displayed for the first time, with two underlying buttons that a user can select. The indicator 216 and buttons allow a user to control the level of defibrillator energy that is delivered by the defibrillator when a shock is delivered. The current level may be reflected on an electronic display such as display 104. Thus, a user may place their right hand at the edge of the defibrillator and squeeze to place their thumb on either the up arrow to increase the energy level, or the down arrow to decrease the energy level. As explained more fully below, a switch may be provided behind the area that the user presses, and light may be provided around the switch. Such light may cause the indicator 216 to transition from essentially invisible to a user from the front of the defibrillator, to fully visible when it is lit.

Indicator 214 shows "ANALYZE" and "CHARGE" options that can be selected by a user pressing on the rectangles that are revealed when lights behind the indicators 214 are lit. When a user presses the CHARGE button, the defibrillator charges to the selected energy. Another charge button may also be placed off the main defibrillator housing, such as on an electrode paddle handle. When a user presses the ANALYZE button, the defibrillator initiates an ECG analysis to determine whether or not a shockable rhythm is present in a victim.

A row of four other indicators 212 allows for further control in a manual or ALS mode, by a presumably advanced and extensively-trained caregiver user. For example, a LEAD indicator/button selects the ECG source that is to be displayed and printed. Pressing this button sequentially selects ECG signals derived from various different lead configurations for display. The SIZE indicator/button selects the amplitude scale by which the ECG will be displayed on the electronic display for the defibrillator. Available sizes can include, for example, 0.5, 1, 1.5, 2, and 3 centimeters per mill volt (cm/mV).

The ALARM SUSPEND indicator/button activates, deactivates, or audibly suspends all alarm functions. A bell symbol appears on an electronic display of the defibrillator when alarms are enabled. When alarms are either audibly or permanently disabled, an "X" appears across the bell symbol.

The RECORDER indicator/button starts or stops a strip chart recorder that is provided with a defibrillator. Pressing and holding the button can switch a defibrillator to diagnostic ECG bandwidth (0.05-150 Hz), and such diagnostic bandwidth may be maintained as long as the RECORDER indicator/button is held down. When the indicator/button is released, the unit reverts to standard monitoring bandwidth.

Thus, by these mechanisms, an initial user may be directed to turn the unit to the ON position because that is the only option that is initially shown to be available to them. A subsequent, more completely trained user may then switch the device to manual mode (and pacing mode), to cause the extra indicators to be displayed under a flat front panel display, and to cause certain switches or buttons that correspond to display locations to be monitored for use input.

Figure 3:
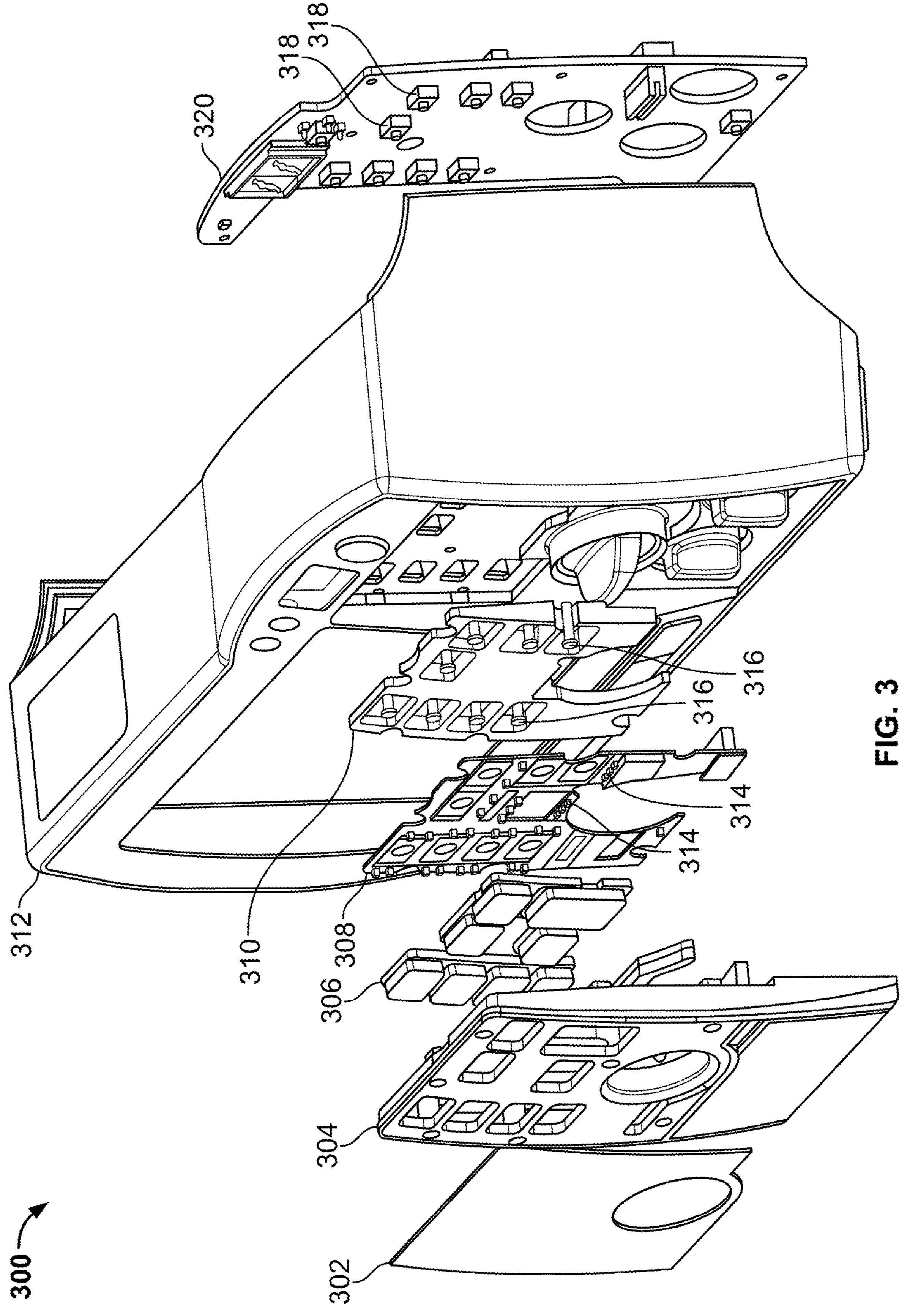
FIG. 3 shows an exploded view of a control and display panel for a dual-mode external defibrillator.

FIG. 3 shows an exploded view of a control and display panel for a dual-mode external defibrillator. In general, the figure shows components that may be employed behind the face of a defibrillator 300 in the display area shown in FIGS. 1A, 1B, and 2A to 2C. Such components may be used to prevent a user of the defibrillator 300 from seeing certain indicators and related buttons when the defibrillator 300 is in a first mode, but to display the indicators when the defibrillator 300 is in a second mode, and when light from inside the defibrillator 300 housing is being transmitted through the face of the display area on the front of the defibrillator 300.

Each of the relevant layers that make up the assembly here will now be discussed, moving from the front of the defibrillator 300 on the left to the inside of the defibrillator 300 housing on the right. The first component in this example is a front panel overlay 302. The overlay 302 may be a multi-layered assembly that includes a thin, relatively flat cover layer such as in the form of a transparent or semi-transparent plastic film or sheet. The cover layer may be backed by a velvet-textured polyester film or similar selectively-transmissive material. On the back of the selectively-transmissive layer, an inked or similarly constructed layer may be provided that defines text or graphics to be displayed to a user when the compartment is provided with light. In this manner, the text or graphics may be hidden when a backing light is not applied to them, in a "dead front" arrangement, and may be visible to a user when light is applied to the back of the overlay 302.

Behind the overlay 302 is a front panel 304. The panel 304 serves to stabilize the overlay, which is flexible, so that it is presented to a user as a relatively flat surface, but so that areas of the overlay can be pressed by a user and depressed slightly to make selections on the surface of the overlay 302. The panel 304 may be an injection molded, relatively rigid, plastic structure that is interrupted in particular locations by through-holes. The through-holes may be positioned so as to correspond to buttons that are represented on the face of the display area of the overlay 302, so that light can pass through the panel 304 in such areas, and a user's inputs may be transmitted back to buttons or other structures via the through-holes into the housing of the defibrillator 300.

A number of flexible tiles 306 may be provided on one or more sheets generally behind the panel 304, but may extend forward through the holes in the panel and be close to, or in contact with, the back side of the overlay 302. The flexible tiles 306 may be made out of a light-transmissive material such as silicone. The panel 304 may also serve to diffuse light that enters it from behind, so that graphics or text displayed to a user on the front of the overlay 302 is more evenly lit.

A flexible circuit board 308 is mounted behind the flexible tiles 306, and may have mounted on it a plurality of light emitting diodes 314. The diodes 314 may be controlled via a microprocessor, memory, and related circuitry and software in the defibrillator 300 so as to light at appropriate times, including with a dependence on the mode in which a user has placed the defibrillator 300. Such lighting may be made according to the standards shown in the figures above. The flexible circuit board 308 may take a variety of appropriate forms, and may be interrupted by various openings in the board where force from a user contacting the front of the overlay 302 may be passed readily to components in the assembly that are further back in the housing for the defibrillator 300 than is the flexible circuit board 308.

Behind the flexible circuit board 308 is an inner frame 310 that, like the front panel 304, is a relatively inflexible injection molded plastic component that serves to support the flexible circuit board 308 from behind, and also has included in it various actuators 316. The actuators 316 are elongated structures that are located in each of the holes of the frame 310 that are aligned with user-selectable buttons on the front of overlay 302. The actuators 316 operate to transmit the force of a user pressing one of the buttons back to pushbutton switches 318 mounted on a circuit board 320 at the back of the assembly. In this manner, the user can obtain favorable feedback and a relatively long throw in pressing selections on the overlay 302, and in certain situations may be provided with clicking or other particular tactile feedback when a selection has been made successfully. Also, an electronic feedback mechanism, such as a vibration or an audible sound on a speaker of the defibrillator 300, may also be provided when a selection has been recognized by the defibrillator 300, in coordination with a microprocessor that registers the selection.

The circuit board 320 may carry a variety of components in addition to the switches 318. For example, light emitting components for the indicators at the top of the defibrillator 300, above the display area, may be provided on the circuit board 320. In addition, various logic circuit, memory, and processors may, in appropriate implementations, be mounted on the circuit board 320. Also, the circuit board 320 may be interrupted in various locations, such as to permit for the positioning of knobs that are accessible from the front of the defibrillator 300 around the area of the various lighted displays that have just been discussed.

Finally, next to the adjustment knobs and the assembly just described is a front panel display 312, which may take the form, for example, of an LED, LCD, OLED, or similar active display, which may provide to a user color graphics that represent instructions to the user and real-time parameters of the defibrillator. The information displayed on the display 312 may be coordinated with the selected mode of the device so that, for example, the display 312 shows only basic instructions when the defibrillator is in BLS mode, and shows more complete data when the defibrillator is in ALS mode.

In this manner, a composite user interface may be provided to a user of a defibrillator, where the interface may include any appropriate combination of active display (which may be a touchscreen display), user-graspable knobs and/or switches, solid user-selectable buttons, and lit-from-behind indicators and/or buttons that display information to a user when the defibrillator is in one mode, but does not show the information to the user when the defibrillator is in another mode or modes.

Figure 4:
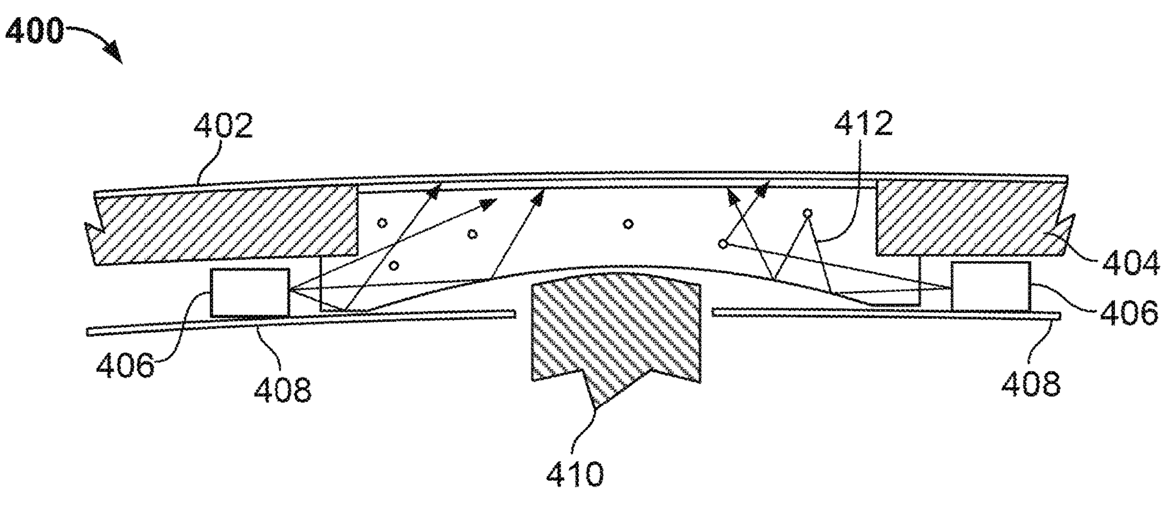
FIG. 4 shows a cross-section of a lighting mechanism for a display on a medical device.

FIG. 4 shows a cross-section of a lighting mechanism 400 for a display on a medical device. The lighting mechanism 400 may include a sub-set of the components shown in FIG. 3, and are shown here in cross-section from above, as the components would be mounted in a defibrillator housing.

Starting from the front of the assembly 400 at the top of the figure, there is a front panel overlay 402. The overlay 402 may include a plurality of layers in order to provide a display that cannot be seen from the front of the overlay when no light is generated behind the overlay, but that is visible when light passes up through the overlay 402. For example, a first layer may simply be a transparent or mostly transparent plastic sheet, which may be as thin as a film or relatively thicker so as to provide appropriate sturdiness and user feel for a user who presses against the overlay 402 in order to activate a feature on a defibrillator or other medical device. The first layer may be backed by a velvet textured polyester film or similar selectively-transmissive material that provides for a "dead front" on the medical device when no light is provided within the particular compartment, i.e., a user can see at most a very faint representation of any text or graphics that are easily visible when a light is provided within the compartment.

On the back of the selectively-transmissive layer, an inked or similarly constructed layer may be provided that defines text or graphics to be displayed to a user when the compartment is provided with light. For example, the layer may show an icon to a user that indicates a status or parameter of the defibrillator. The layer may also include text that provides additional notification to a user, including an indication that the parameter can be affected by the user pressing on the particular area. For example, an icon shaped like an arrow may indicate to a user that pressing on the icon will cause a related parameter to be increased or decreased by a microprocessor that is operating on the device.

A front panel 404 is provided to support the overlay and also to define a plurality of essential light-tight compartments, where each compartment corresponds to a key and/or indicator area on the front of the device. The compartments may, in particular, enable selective visibility of particular areas on a front panel of a display like the display on front overlay 302 in FIG. 3, based upon selective energizing of light sources behind the display.

The compartments in the front panel 404 may be filled with respective portions of silicone tiles 412, so that light can pass through the tiles 412 and thus through the openings and compartments in the front panel 404. The silicone tiles may be provided, on the back edges (at the bottom of FIG. 4) with a reflective layer made of paint or a reflective film (e.g. white Mylar) that is adhesively applied to the silicone. The reflective layer causes light that enters the silicone tiles 412 to be reflected forward through the compartments through overlay 402 and out the front of the device so that a user of the device can view text or graphics that are on the overlay 402. Also, paint pigment may be provided within the silicon tiles 412 to further enhance dispersion of the light within the tiles 412 so as to provide a more even lighting of the various areas that overlay the compartments, and which the user can see from the front of the device.

LED lights 406 or other similar light sources are provided on each side of a silicon tile 412 so that, when the LED lights 406 are energized, their light can enter the tile 412 from the sides that are in front of the reflective layer, and the light may then be directed upward through the overlay 402 so that a user of the device can see the printed graphics and text, as appropriate. The lights 406 may be shared between compartments or blocked between compartments as appropriate to provide a user with a proper interface, and so that functions that are not currently available on the device (in its currently-selected operation mode) are not shown to a user of the device. In this example, the lights 406 are mounted directly to the front of a circuit board 408 which carries electrical energy to the lights.

In other embodiments, a central light source may be provided and light pipes or other similar structures may be provided to direct light to an appropriate compartment. Light valves may also be provided in such situations so as to control which compartments receive light. A microprocessor on a device may coordinate the switching of such valves or the powering of lights 406 so as to provide for an appropriate user interface that is coordinated with the current feature set of a defibrillator or other medical device.

An actuator 410 is positioned behind the silicon tile 412 and is pushed downward when a user of the device pushes on the front of the overlay 402 in the position located over the appropriate compartment. The actuator 410 may be connected directly to a switch that is actuated by the user pressing downward in the appropriate zone, or may be in contact with the switch. The actuator may be guided and held in place by a structure such as the inner frame 310 of the defibrillator 300 in FIG. 3.

In this manner, a "dead front" display may be provided on a portion of a medical device such as a defibrillator. The dead front may be dead when the device is in a first mode, such as a basic operational mode that is designed for relatively untrained users, and may be lit up and active when the device is in a second mode, such as an advanced operational mode that is designed for relatively highly trained users.

Figure 5:
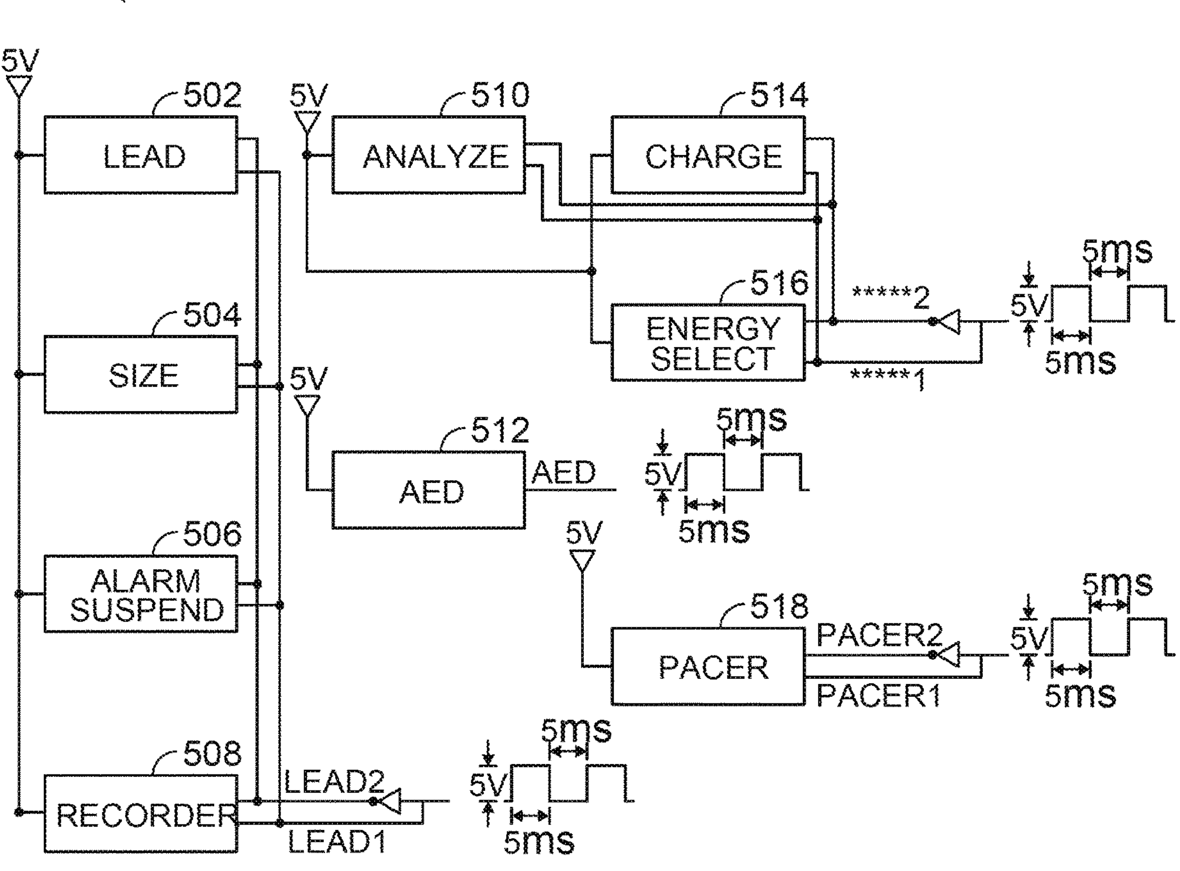
FIG. 5 is a schematic diagram of a lighting circuit for a dual-mode medical device.

FIG. 5 is a schematic diagram of a lighting circuit for a dual-mode medical device. In this example, LEDs are organized into four groups. The first group, involving AED light 512, lights the wording of "AED" on the front of a defibrillator when the defibrillator is in AED, or BLS, mode. The second group, consisting of lead light 502, size light 504, alarm suspend light, and recorder light 508, are energized or de-energized in unison, and are lit when the defibrillator is in manual or ALS mode. The third group, consisting of the analyze light 510, charge light 514, and energy select light 516, are lit when the defibrillator is in manual mode. The fourth group, which is the pacer light 518, is lit—in addition to the lights in the second and third groups, when the device is in the pacer mode. Each of the sets of lights may be energized under the control of a microprocessor operating in a medical device (in cooperation with memory, and instructions stored in the memory and executed by the microprocessor) in a manner that the lights are energized when the device is in an appropriate mode—where the mode is responsive to inputs or outputs corresponding to the lit features when those features are lit, and is not responsive when the features are not lit.

Power to the lights, when it is supplied, is supplied in alternating 5 ms increments, as shown in the figure. Certain of the lighting sub-groups include alternating subgroups of LEDs, provided in combination with switching functionality, and the switching of the control voltage is switched quickly enough that the human eye does not discern the switching.

Figure 6:
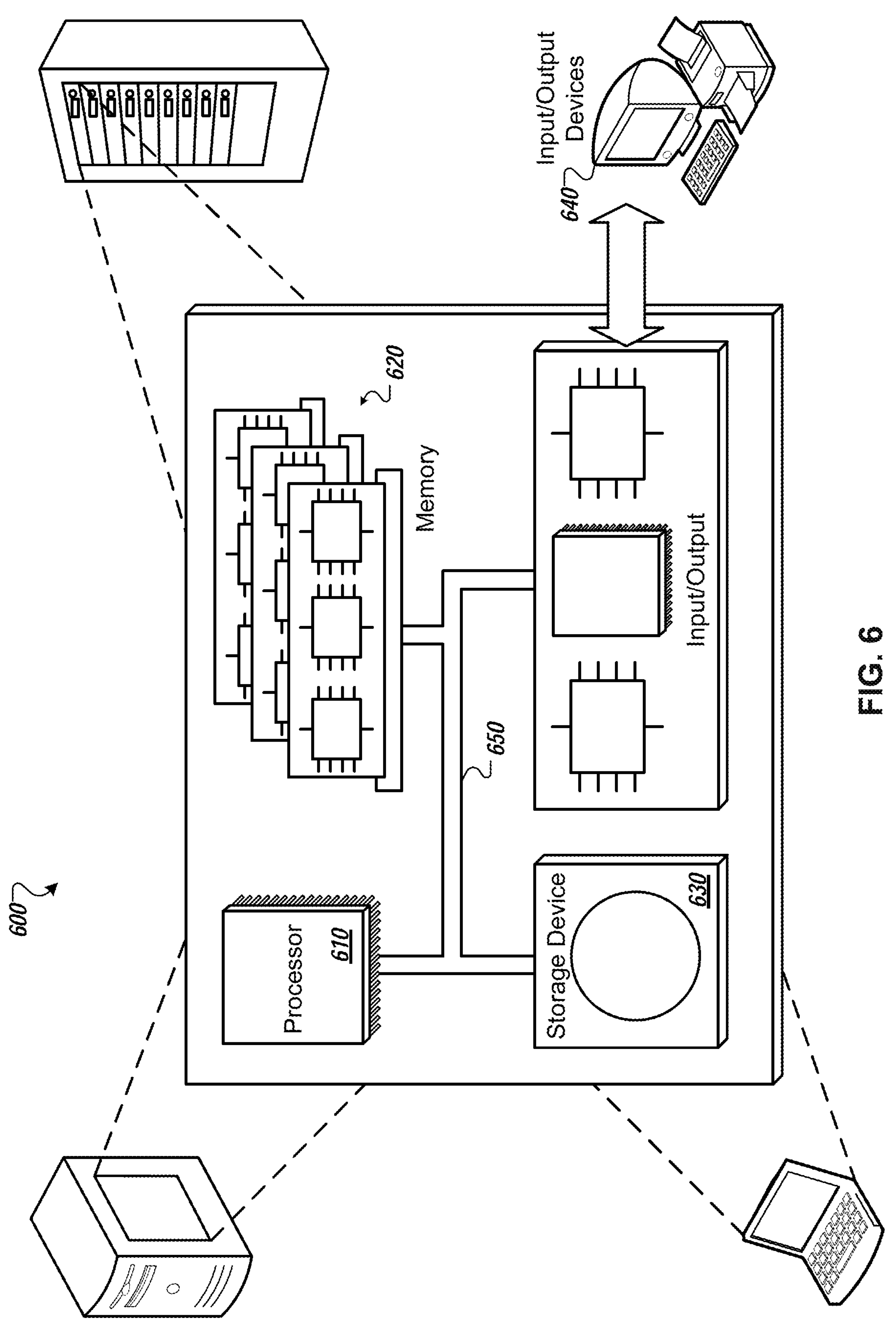
FIG. 6 is a schematic diagram of a general computing system that can be employed to operate a medical device in manners like those discussed here.

FIG. 6 is a schematic diagram of a computer system 600. The system 600 can be used for the operations described in association with any of the computer-implement methods described previously, according to one implementation, such as in changing the electronic mode of a medical device and presenting information on a display screen of an electronic device. The system 600 may take a variety of general forms, as shown, though its preferred form here is as a portable medical device. Additionally the system can include portable storage media, such as, Universal Serial Bus (USB) flash drives. For example, the USB flash drives may store operating systems and other applications. The USB flash drives can include input/output components, such as a wireless transmitter or USB connector that may be inserted into a USB port of another computing device. The system 600 includes a processor 610, a memory 620, a storage device 630, and an input/output device 640. Each of the components 610, 620, 630, and 640 are interconnected using a system bus 650. The processor 610 is capable of processing instructions for execution within the system 600. The processor may be designed using any of a number of architectures. For example, the processor 610 may be a CISC (Complex Instruction Set Computers) processor, a RISC (Reduced Instruction Set Computer) processor, or a MISC (Minimal Instruction Set Computer) processor.

In one implementation, the processor 610 is a single-threaded processor. In another implementation, the processor 610 is a multi-threaded processor. The processor 610 is capable of processing instructions stored in the memory 620 or on the storage device 630 to display graphical information for a user interface on the input/output device 640.

The memory 620 stores information within the system 600. In one implementation, the memory 620 is a computer-readable medium. In one implementation, the memory 620 is a volatile memory unit. In another implementation, the memory 620 is a non-volatile memory unit.

The storage device 630 is capable of providing mass storage for the system 600. In one implementation, the storage device 630 is a computer-readable medium. In various different implementations, the storage device 630 may be a floppy disk device, a hard disk device, an optical disk device, or a tape device. The input/output device 640 provides input/output operations for the system 600. In one implementation, the input/output device 640 includes a keyboard and/or pointing device. In another implementation, the input/output device 640 includes a display unit for displaying graphical user interfaces.

The features described can be implemented in digital electronic circuitry, or in computer hardware, firmware, software, or in combinations of them. The apparatus can be implemented in a computer program product tangibly embodied in an information carrier, e.g., in a machine-readable storage device for execution by a programmable processor; and method steps can be performed by a programmable processor executing a program of instructions to perform functions of the described implementations by operating on input data and generating output. The described features can be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Suitable processors for the execution of a program of instructions include, by way of example, both general and special purpose microprocessors, and the sole processor or one of multiple processors of any kind of computer. Generally, a processor will receive instructions and data from a read-only memory or a random access memory or both. The essential elements of a computer are a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM and DVD-ROM disks. The processor and the memory can be supplemented by, or incorporated in, ASICs (application-specific integrated circuits).

To provide for interaction with a user, the features can be implemented on a computer having a display device such as a CRT (cathode ray tube) or LCD (liquid crystal display) monitor for displaying information to the user and a keyboard and a pointing device such as a mouse or a trackball by which the user can provide input to the computer.

The features can be implemented in a computer system that includes a back-end component, such as a data server, or that includes a middleware component, such as an application server or an Internet server, or that includes a front-end component, such as a client computer having a graphical user interface or an Internet browser, or any combination of them. The components of the system can be connected by any form or medium of digital data communication such as a communication network. Examples of communication networks include a local area network ("LAN"), a wide area network ("WAN"), peer-to-peer networks (having ad-hoc or static members), grid computing infrastructures, and the Internet.

The computer system can include clients and servers. A client and server are generally remote from each other and typically interact through a network, such as the described one. The relationship of client and server arises by virtue of computer programs running on the respective computers and having a client-server relationship to each other.

A number of embodiments have been described. Nevertheless, it will be understood that various modifications may be made without departing from the spirit and scope of the invention. For example, much of this document has been described with respect to defibrillators as medical devices, though other medical devices may employ the features described here. Also, although the modes described above are generally basic and advanced modes, the modes could also be language specific, so that portions of a display in one language could be lit in a first mode, and portions for a second language could be lit in a second mode, where the user of a device may use a knob or touchscreen interface, or other appropriate input mechanism, to select the desired mode. Also, different textual or graphical labels may be provided and swapped out in a device, so that the language for a device may be changed manually as appropriate.

Accordingly, other embodiments are within the scope of the following claims.

What is claimed is:

1. A computer implemented method of controlling a defibrillator, the method comprising:

receiving, via a user interface of the defibrillator, a selection of a display mode for the defibrillator, the selection specifying either a basic life support mode or an advanced life support mode;

based at least in part upon the selection specifying the basic life support mode, controlling a display of the defibrillator to show one or more first indicators that provide basic life support information, the one or more first indicators including graphics indicating electrode application to a patient;

based at least in part upon the selection specifying the advanced life support mode, controlling the display to show one or more second indicators and one or more third indicators, the one or more second indicators being selectable to provide text or graphics related to pacing and the one or more third indicators being selectable to provide text or graphics related to a time of performing cardiopulmonary resuscitation (CPR) and text or graphics related to changing a level of energy to be applied to electrodes of the defibrillator, and controlling the display to not show the one or more first indicators that provide graphics indicating electrode application to a patient; and delivering a therapeutic shock while the display mode is in either the basic life support mode or the advanced life support mode.

2. The computer implemented method of claim 1, wherein:

the selection specifies the advanced life support mode; and the method further comprises accessing additional information about the defibrillator or changing parameters that control the defibrillator.

3. The computer implemented method of claim 1, wherein:

the user interface comprises at least one button; and the method further comprises controlling treatment provided by the defibrillator via activation of the at least one button.

4. The computer implemented method of claim 1, wherein:

the user interface comprises the display;

the display comprises a touchscreen; and the method further comprises receiving a touchscreen input on the touchscreen, wherein the touchscreen input controls display of information of the defibrillator.

5. The computer implemented method of claim 1, wherein:

the selection specifies the advanced life support mode; and controlling the display of the defibrillator to show the one or more second indicators and the one or more third indicators comprises controlling the display of the defibrillator to show one or more features of the defibrillator available in advanced life support mode.

6. The computer implemented method of claim 1, wherein controlling the display of the defibrillator to show the one or more second indicators and the one or more third indicators further comprises controlling the display of the defibrillator to show at least one of: an electrocardiogram (ECG), a graph of cardiopulmonary resuscitation (CPR) chest compressions administered, a pulse, or information regarding one or more electrodes applied to a patient.

7. The computer implemented method of claim 1, wherein the method further comprises not showing at least a portion of the one or more second indicators based at least in part upon the selection specifying the basic life support mode.

8. The computer implemented method of claim 7, wherein not showing the at least a portion of the one or more second indicators comprises not showing at least one of: "Lead", "Size", "Alarm Suspend", "Recorder", "Analyze", "Charge", "Energy Select", "Pacer", or one or more arrows.

9. The computer implemented method of claim 1, wherein the method further comprises making unavailable one or more controls corresponding to the advanced life support mode, based at least in part upon the selection specifying the basic life support mode.

10. The computer implemented method of claim 9, wherein making unavailable the one or more controls corresponding to the advanced life support mode comprises making unavailable one or more user-selectable buttons.

11. The computer implemented method of claim 1, wherein the method further comprises not showing the text or graphics related to pacing, based at least in part upon the selection specifying the basic life support mode.

12. The computer implemented method of claim 11, wherein not showing the text or graphics related to pacing comprises hiding at least one of: pace rate or electrode power output.

13. The computer implemented method of claim 1, wherein the method further comprises making unavailable notifications or warnings corresponding to the advanced life support mode, based at least in part upon the selection specifying the basic life support mode.

14. The computer implemented method of claim 1, wherein:

the selection specifies the basic life support mode; and controlling the display of the defibrillator to show the one or more first indicators further comprises controlling the display of the defibrillator to show the one or more first indicators that are simpler than the one or more second indicators or the one or more third indicators.

15. The computer implemented method of claim 1, wherein controlling the display of the defibrillator to show the one or more first indicators comprises controlling the display of the defibrillator to show the one or more first indicators that provide at least one of: automated external defibrillator (AED) information, instructions to guide a user in providing life support, instructions to apply electrodes to a patient, or instructions to perform CPR.

16. The computer implemented method of claim 15, wherein controlling the display of the defibrillator to show the one or more first indicators that provide the instructions to perform CPR comprises controlling the display of the defibrillator to show the one or more first indicators that provide at least one of: instructions to push harder, instructions to push softer, instructions to provide CPR faster, and instructions to provide CPR slower.

17. The computer implemented method of claim 1, wherein receiving the selection specifying the basic life support mode comprises receiving a selection specifying an AED mode.

18. The computer implemented method of claim 1, wherein receiving the selection specifying the advanced life support mode comprises receiving a selection specifying a manual mode.

19. The computer implemented method of claim 1, wherein the user interface comprises a mechanical mechanism, and wherein receiving the selection of the display mode for the defibrillator comprises receiving the selection via the mechanical mechanism.

20. The computer implemented method of claim 1, wherein the method further comprises, in response to the selection specifying the advanced life support mode, activating one or more light sources arranged behind a layer having printed text and/or graphics.

* * * * *